United States Patent
Xu et al.

(10) Patent No.: US 11,976,300 B2
(45) Date of Patent: May 7, 2024

(54) USE OF WATER-SOLUBLE REALGAR SOLID DISPERSION IN PREPARATION OF ERYTHROID DIFFERENTIATION INDUCER FOR BONE MARROW HEMATOPOIETIC STEM CELLS AND/OR BONE MARROW HEMATOPOIETIC PROGENITOR CELLS

(71) Applicant: Institute of Basic Medical Sciences Chinese Academy of Medical Sciences, Beijing (CN)

(72) Inventors: Haiyan Xu, Beijing (CN); Jian Liu, Beijing (CN); Tao Wang, Beijing (CN); Bing Han, Beijing (CN); Jie Meng, Beijing (CN); Tao Wen, Beijing (CN)

(73) Assignee: INSTITUTE OF BASIC MEDICAL SCIENCES CHINESE ACADEMY OF MEDICAL SCIENCES, Beijing (CN)

( * ) Notice: Subject to any disclaimer, the term of this patent is extended or adjusted under 35 U.S.C. 154(b) by 833 days.

(21) Appl. No.: 17/046,383

(22) PCT Filed: Apr. 11, 2019

(86) PCT No.: PCT/CN2019/082256
§ 371 (c)(1),
(2) Date: Oct. 9, 2020

(87) PCT Pub. No.: WO2019/196903
PCT Pub. Date: Oct. 17, 2019

(65) Prior Publication Data
US 2021/0155901 A1      May 27, 2021

(30) Foreign Application Priority Data
Apr. 11, 2018   (CN) .......................... 201810321323.9

(51) Int. Cl.
| | | |
|---|---|---|
| C12N 5/078 | (2010.01) | |
| A61K 9/14 | (2006.01) | |
| A61K 33/36 | (2006.01) | |
| A61P 7/00 | (2006.01) | |
| A61P 7/02 | (2006.01) | |
| A61P 7/06 | (2006.01) | |
| A61P 35/02 | (2006.01) | |

(52) U.S. Cl.
CPC ............ *C12N 5/0641* (2013.01); *A61K 9/146* (2013.01); *A61K 33/36* (2013.01); *A61P 7/00* (2018.01); *A61P 7/02* (2018.01); *A61P 7/06* (2018.01); *A61P 35/02* (2018.01); *C12N 2501/999* (2013.01); *C12N 2506/1353* (2013.01)

(58) Field of Classification Search
CPC ............ C12N 5/0641; C12N 2501/999; C12N 2506/1353; A61P 7/06; A61P 7/00; A61P 7/02; A61P 35/02; A61K 9/146; A61K 33/36
See application file for complete search history.

(56) References Cited

FOREIGN PATENT DOCUMENTS

| | | | | | |
|---|---|---|---|---|---|
| CA | 2328165 | A1 * | 11/1999 | ............. | A61K 33/66 |
| CN | 1299668 | C  * | 2/2007 | ............... | A61K 9/14 |
| CN | 106236773 | A  * | 12/2016 | ............. | A61K 33/66 |

* cited by examiner

*Primary Examiner* — Shirley V Gembeh
*Assistant Examiner* — Olga V. Tcherkasskaya
(74) *Attorney, Agent, or Firm* — Scully, Scott, Murphy & Presser, P.C.

(57) ABSTRACT

Disclosed is the use of a water-soluble realgar solid dispersion in the preparation of an erythroid differentiation inducer for bone marrow hematopoietic stem cells and/or bone marrow hematopoietic progenitor cells. The water-soluble realgar solid dispersion is prepared from raw materials comprising 1 part by weight of realgar, 1-20 parts by weight of a polymer, and 0-5 parts by weight of a surfactant. The water-soluble realgar solid dispersion can induce bone marrow hematopoietic stem and/or progenitor cells to be differentiated into red blood cells, promote the accumulation of red blood cells in bone marrow cells, effectively alleviate the decrease in the number of red blood cells caused by the suppression of the erythroid differentiation of bone marrow hematopoietic stem and/or progenitor cells, improve anemia caused by hematopoietic failure, and protect bone marrow cells from the killing effect.

4 Claims, 6 Drawing Sheets

USE OF WATER-SOLUBLE REALGAR SOLID DISPERSION IN PREPARATION OF ERYTHROID DIFFERENTIATION INDUCER FOR BONE MARROW HEMATOPOIETIC STEM CELLS AND/OR BONE MARROW HEMATOPOIETIC PROGENITOR CELLS

TECHNICAL FIELD

This invention is related to the field of medicine, in particular to use of water-soluble realgar solid dispersion in preparation of erythroid differentiation inducer for bone marrow hematopoietic stem cells and/or bone marrow hematopoietic progenitor cells.

BACKGROUND TECHNIQUE

Bone marrow is the hematopoietic tissue in human body, locating in the medullary cavity of long bones and all cancellous bones. There are two types of adult human bone marrow: red one and yellow one. The red bone marrow produces erythrocytes, platelets and various leukocytes. Platelets have a hemostatic effect, and leukocytes can kill and inhibit various pathogens, including bacteria and viruses. There are bone marrow mononuclear cells in the bone marrow, mainly including bone marrow hematopoietic stem cells and/or progenitor cells, monocytes and lymphocytes. Among these cells, bone marrow hematopoietic stem cells and/or bone marrow hematopoietic progenitor cells, also named as bone marrow hematopoietic cells, have hematopoietic function and can differentiate towards erythrocytes. If the differentiation process (i.e., erythroid differentiation) is blocked, a reduction in the number of erythrocytes in the bone marrow and peripheral blood will occur, which causes anemia. It is known that many diseases lead to the blockade of erythroid differentiation of bone marrow hematopoietic cells, such as myelodysplastic syndrome (MDS), aplastic anemia, chronic myelomonocytic leukemia and chronic myeloid leukemia, thereby causing anemia that has severe adverse effects on the treatment efficacy and life quality of patients.

The treatment strategy for blocked erythroid differentiation of bone marrow hematopoietic cells and/or progenitor cells is to induce bone marrow hematopoietic cells and/or progenitor cells to differentiate towards erythrocytes by using certain drugs. At present, drugs to stimulate the differentiation and proliferation of bone marrow hematopoietic cells and/or progenitor cells towards erythrocytes is mainly recombinant human erythropoietin (EPO), which was discovered in 1984 and applied in treating anemia for the first time in 1986, which could increase erythrocytes and hemoglobin, thereby relieving anemia to patients. However, EPO also brings severe toxic side effects in clinic application. In addition to EPO, reports of other drugs are very limited.

Hence, there is an urgent need in this field to develop medicines that can induce erythroid differentiation of bone marrow hematopoietic cells and/or progenitor cells with lower toxic side effects.

SUMMARY OF THE INVENTION

The aim of the present invention is to provide applications of water-soluble realgar solid dispersions in the preparation of inducers for uses in the induction of erythroid differentiation of bone marrow hematopoietic stem cell and/or progenitor cell, in view of the technical defects existing in prior arts. The water-soluble realgar solid dispersion was prepared with raw materials comprising 1 weight part realgar, 1-20 weight parts polymers and 0-5 weight parts surfactants.

Said realgar refers to refined realgar (abbreviated as r-$As_4S_4$, the chemical composition is $As_4S_4$), and the particle size was 20-75 μm.

The polymer was selected from amphiphilic polymers, specifically one or more of the followings: polyethylene glycol-polyvinyl alcohol graft copolymer, polyvinyl pyrrolidone (PVP), cross-linked polyvinylpyrrolidone (PVPP), polyvinylcaprolactam-polyvinyl acetate-polyethylene glycol graft copolymer, poly (vinyl pyrrolidone-co-vinyl acetate) (PVP-VA) and Poloxamer.

The surfactants may be nonionic surfactants or ionic surfactants.

The surfactant is selected from one or more of the followings: polysorbate 20, polysorbate 60, polysorbate 80, sodium dodecyl sulfate, polyethylene glycol cetostearyl ether and sodium cetostearyl sulfate.

The active ingredient in the water-soluble realgar solid dispersion is $As_4S_4$, and the polymers act as the dispersion matrix.

The solid dispersion can rapidly disintegrate in water to form stable yellow colloidal solution that contains realgar nanoparticles encapsulated by the polymer. The hydrated particle size of realgar nanoparticles ranged from 1 to 1000 nm, preferably from 100 to 1000 nm.

In artificial gastric juice, the cumulative dissolution rate of $As_4S_4$ from the water-soluble realgar solid dispersion was 9%-25%.

The inducers for erythroid differentiation of bone marrow hematopoietic cells and/or progenitor cells are used as the drugs for the treatment of diseases caused by blocked erythroid differentiation of bone marrow hematopoietic cells and/or progenitor cells. The disease is characterized by anemia, mainly including myelodysplastic syndrome (MDS), myelodysplastic syndrome-refractory anemia (MDS-RA), myelodysplastic syndrome-refractory anemia with ringed sideroblasts (MDS-RARS), myelodysplastic syndrome-refractory anemia with excess blasts (MDS-RAEB), myelodysplastic syndrome-refractory anemia with excess blasts-transformation (MDS-RAEB-T), aplastic anemia, chronic myeloproliferative diseases, chronic myelomonocytic leukemia, chronic myelomonocytic leukemia (CMML), chronic myeloid leukemia (CML), thrombocytosis and thrombocytopenia caused by blocked erythroid differentiation of bone marrow hematopoietic cells and/or progenitor cells.

When water-soluble realgar solid dispersion was used to induce erythroid differentiation of bone marrow hematopoietic cells and/or progenitor cells, the concentration of $As_4S_4$ would be not less than 0.1 mg/L, preferably 0.1-8 mg/L, more preferably 0.1-4 mg/L.

Compared with prior art, the present invention has following benefits:

In the present invention, the water-soluble realgar solid dispersion disclosed in the patent application with the publication No. CN106236773A is used. Specifically, r-$As_4S_4$, the polymer, and the surfactant were added to a twin-screw extruder for co-extrusion by hot melting to obtain a water-soluble realgar solid dispersion (e-$As_4S_4$). The e-$As_4S_4$ prepared by the method can be disintegrated rapidly in water, while the particle size of realgar in the dispersion is significantly reduced as compared with realgar, and can enter the water phase as the polymer dissolves to form polymer-encapsulated realgar nanoparticles in the water, which are uniformly and stably dispersed in the water phase.

The present invention discloses that the water-soluble realgar solid dispersion is incubated with bone marrow mononuclear cells derived from patient or normal human bone marrow to detect the level of the erythroid differentiation marker molecule CD235a on the cell surface. It is found that CD235a on the cell surface was significantly increased in a dose-dependent manner, indicating that e-As4S4 can effectively induce bone marrow hematopoietic cells in bone marrow mononuclear cells to differentiate into erythrocyte. In addition, it has the effect of inducing bone marrow hematopoietic stem cells and/or progenitor cells to differentiate into erythrocyte to both bone marrow-derived bone marrow mononuclear cells and normal bone marrow-derived bone marrow mononuclear cells from the patients with pancytopenia of myelodysplastic syndrome (MDS), myelodysplastic syndrome-refractory anemia (MDS-RA), myelodysplastic syndrome-refractory anemia with ringed sideroblasts (MDS-RARS), myelodysplastic syndrome-refractory anemia with excess blasts (MDS-RAEB), myelodysplastic syndrome-refractory anemia with excess blasts-transformation (MDS-RAEB-T), chronic myeloproliferative diseases, chronic myelomonocytic leukemia (CMML), chronic myeloid leukemia (CML), thrombocytosis, thrombocytopenia, etc. The induction effect can not only effectively relieve the reduction of erythrocytes caused by the blocked erythroid differentiation of bone marrow hematopoietic cells and/or progenitor cells, but also effectively increase the number of erythrocytes in the bone marrow and peripheral blood to relieve the symptoms of anemia. Besides, since the water-soluble realgar solid dispersion has good dispersibility in water and high bioavailability, e-$As_4S_4$ could increase the number of erythrocytes and hemoglobin in low and medium doses with increasing hemoglobin, therefore protecting bone marrow cells from being killed and to avoid systemic side effects caused by large doses of drugs.

DETAILED DESCRIPTION

Realgar is an arsenic-containing mineral drug and its chemical component is $As_4S_4$. Chinese herbal compound realgar-indigo naturalis formula (RIF) has been used as a second-line drug for the initial treatment of acute promyelocytic leukemia in clinically. The mechanism of RIF is considered that indirubin and tanshinone act as adjuvant ingredients to increase the expression of Aquaglyceroporin 9, which makes $As_4S_4$ in the compound enter more leukemia cells, thereby increasing the lethality of $As_4S_4$ on leukemia cells. (Wang L, Zhou G B, Liu P, et al. Dissection of mechanisms of Chinese medicinal formula Realgarindigo naturalis as an effective treatment of promyelocytic leukemia. Proc Natl Acad Sci USA 105: 4826-4831, 2008). Currently, knowledge of main stream on mechanisms of $As_4S_4$ in leukemia treatment is that $As_4S_4$ kills leukemia cells, main opinion believing that $As_4S_4$ dissolved in NaOH solution caused the degradation of the BCR-ABL fusion protein in CML cells through binding to E3 ubiquitin ligases, thereby leading to apoptosis of the leukemia cells (Li J E, Wu W L, Wang Z Y, et al. Apoptotic effect of $As_2S_2$ on K562 cells and its mechanism [J]. Acta Pharmacologica Sinica, 2002, 23(11): 991-996).

Realgar is difficult to dissolve in water or acidic aqueous solution; hence its bioavailability is extremely low. In order to improve the dissolution rate of realgar in water and its bioavailability, and to reduce its safety risks and economic pressure, the inventors invented e-$As_4S_4$ in 2015 (publication number: CN106236773A) and obtained that e-$As_4S_4$ significantly improved the killing effect of $As_4S_4$ on acute promyelocytic leukemia cell line HL60 and chronic myeloid leukemia cell line K562. When the concentration of $As_4S_4$ (hydrodynamic diameter ranged from 100 nm to 1000 nm) reached 41.7 mg/L and 166.7 mg/L the cells would die in large numbers to exert their killing effect. That is, this patent application is based on the killing mechanism of realgar on leukemia cells for the treatment of leukemia. e-$As_4S_4$ at low or medium concentrations only shows medium to low killing effect on leukemia cells. However, the inventor obtained unexpected results in further research: e-$As_4S_4$ at low or medium concentrations could effectively induce erythroid differentiation of bone marrow mononuclear cells derived from bone marrow of patients with different diseases and from that of people without the diseases. In other words, e-$As_4S_4$ could induce bone marrow hematopoietic cells in bone marrow mononuclear cells to differentiate towards erythrocytes, therefore e-$As_4S_4$ could be a therapeutics for treating the diseases related to blocked erythroid differentiation through increasing the number of erythrocytes. This directional induction differentiation function would benefit bone marrow hematopoietic cells in the bone marrow mononuclear cells with blocked erythroid to differentiate towards erythroid, at the same time, would make the patients avoid severe side effects caused by high-dose drugs based on cell killing mechanism, since reducing the drug dosage amount.

It is especially important that only hydrophilic realgar solid dispersion is capable of directed inducing erythroid differentiation of bone marrow hematopoietic cells, while r-$As_4S_4$ is not. So far, there are no publications or patent applications reporting that single or compound realgar or hydrophilic realgar solid dispersion could induce erythroid differentiation of bone marrow hematopoietic stem cells and/or progenitor cells, and no publications or patent applications reporting that realgar could be used to treat anemia caused by blocked erythroid differentiation of hematopoietic stem cells and/or progenitor cells.

The present invention aims to providing applications of e-$As_4S_4$ in preparing inducers for uses in the induction of erythroid differentiation of bone marrow hematopoietic stem cells and/or bone marrow hematopoietic progenitor cells.

The inducers for uses in the induction of erythroid differentiation of bone marrow hematopoietic stem cell and/or progenitor cell in the present invention could be used as drugs for the treatment of diseases caused by the blocked erythroid differentiation of bone marrow hematopoietic cells in bone marrow mononuclear cells. The types of diseases are characterized by anemia. Diseases caused by the blocked erythroid differentiation of bone marrow hematopoietic cells and/or progenitor cells include myelodysplastic syndrome (MDS), aplastic anemia, chronic myelomonocytic leukemia and chronic myeloid leukemia, etc.

The e-$As_4S_4$ related in the present invention is based on the Chinese herbal raw materials—realgar as the active ingredients, and the amphiphilic polymer as the dispersion matrix, composed of 1 part by weight of r-$As_4S_4$ (that is realgar can be directly used as the clinical drugs, of which the particle size is between 20-75 μm, 1-20 parts by weight of polymers as dispersion matrix, 0-5 parts by weight of surfactants.

The polymers acting as dispersion matrix include one or more of the following amphiphilic polymers: polyethylene glycol-polyvinyl alcohol graft copolymer, polyvinyl pyrrolidone (PVP), cross-linked polyvinylpyrrolidone (PVPP), polyvinylcaprolactam-polyvinyl acetate-polyethylene glycol graft copolymer (Soluplus), poly (vinyl pyrrolidone-co-vinyl acetate) (PVP-VA) and poloxamer Poloxamer.

The surfactant could be nonionic or ionic, and specifically was any of the followings: Polysorbate 20, Polysorbate 60, Polysorbate 80, sodium dodecyl sulfate, polyethylene glycol cetostearyl ether and sodium cetostearylsulfate.

The e-$As_4S_4$ was prepared by adding Chinese herbal raw material r-$As_4S_4$, amphiphilic polymer and surfactant into a twin-screw extruder (Haake MiniLab II (Thermo Fisher Scientific, Karlsruhe, Germany) for co-extrusion by hot-melting. Upon the extrusion, shearing and frictional forces are generated by the twin screw in a mixing process, large crystalline particles of r-$As_4S_4$ are squeezed to nanoparticles and dispersed uniformly in the polymer matrix to form the solid dispersion (e-$As_4S_4$). The obtained e-$As_4S_4$ could disintegrate rapidly in water; the realgar in the dispersion can be dissolved with the dissolution of the polymer to form the realgar nanoparticles encapsulated by the polymer. Therefore, the prepared water-soluble realgar solid dispersion can be uniformly and stably dispersed in the water phase. As a result, the dissolution and bioavailability of realgar in aqueous solutions are greatly improved. Furthermore, r-$As_4S_4$ can be used directly in this method, no need to have it nano-processed in advance, which therefore can avoid the generation of toxic by-products easily generated during conventional nano-process.

The e-$As_4S_4$ can refer to the content disclosed in CN106236773A, and specific water-soluble realgar solid dispersion used in the present invention and its preparation process are shown in the following examples.

The present invention will be explained and demonstrated more detailed with following specific embodiments, but these embodiments are not intended to limit the invention.

EMBODIMENTS

The e-$As_4S_4$ used in Embodiments 1-10 was prepared by following approaches, only the composition of the raw materials and preparation process parameters were adjusted among the ten embodiments. The processing parameters are shown in Table 1 (mentioned in Table 1). The preparation process is: certain weight of r-$As_4S_4$ and polymers (and surfactants) were mixed in a container at first, the mixture was then added into the extruder. The temperature inside the extruder was set to 50-200° C., and the screw speed was set to 5-100 r/min. The mixture was extruded from the die orifice and cooled down to the room temperature to obtain a yellow solid product.

TABLE 1

Raw material composition and preparation process parameters of e-As$_4$S$_4$

| | Polymers | | Raw realgar | | Preparation process parameters | |
|---|---|---|---|---|---|---|
| | | | | | Extruder | |
| Embodiments | Type | Weight (g) | Weight (g) | Surfactant (g) | temperature (° C.) | Screw speed (r/min) |
| Embodiment 1 | Polyethylene glycol-polyvinyl alcohol graft copolymer | 3 | 1 | — | 50 | 30 |
| Embodiment 2 | PVP | 4 | 1 | — | 170 | 5 |
| Embodiment 3 | PVPP | 12 | 1 | — | 150 | 50 |
| Embodiment 4 | Polyvinyl caprolactam-polyvinyl acetate-polyethylene glycol graft copolymer | 2 | 2 | — | 100 | 20 |
| Embodiment 5 | Polyvinyl caprolactam-polyvinyl acetate-polyethylene glycol graft copolymer | 6 | 1 | Polysorbate 20, 3 | 90 | 70 |
| Embodiment 6 | Polyvinyl caprolactam-polyvinyl acetate-polyethylene glycol graft copolymer | 9 | 1 | Sodium dodecyl sulfate, 5 | 120 | 100 |
| Embodiment 7 | PVP-VA 64 | 9 | 1 | — | 140 | 40 |
| Embodiment 8 | PVP-VA 64 | 15 | 1 | — | 200 | 50 |
| Embodiment 9 | PVP-VA 64 | 8 | 1 | Polyethylene glycol cetyl stearyl ether, 1 | 180 | 80 |
| Embodiment 10 | Poloxamer 188 | 2 | 1 | — | 90 | 10 |

Figure 1:
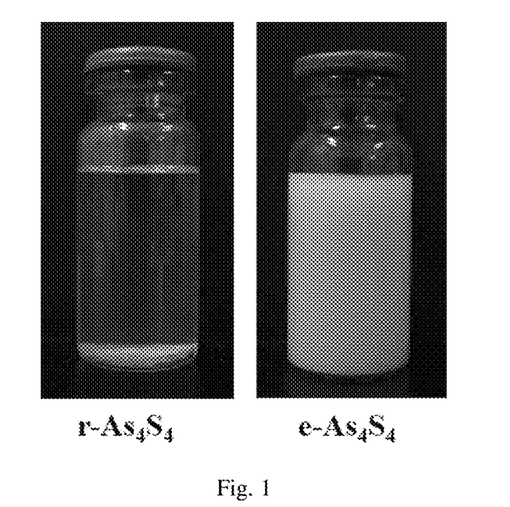
FIG. 1 is the comparison diagram of the realgar raw material drug and the water-soluble realgar solid dispersion used in the present invention in water dispersion.

Experimental Example 1: Evaluation of Water Solubility 1.500 grams of e-As$_4$S$_4$ of Embodiment 5 and 100 mg of the r-As$_4$S$_4$ powder were weighed and added in 10 mL of double distilled water (ddH$_2$O), respectively to obtain the water dispersion solution of e-As$_4$S$_4$ and r-As$_4$S$_4$. The appearance of the suspensions was shown in FIG. 1.

It was shown that e-As$_4$S$_4$ was able to dissolve in ddH$_2$O rapidly, and realgar entered the water phase in a larger amount with a significantly increased dissolution rate and formed a yellow colloid solution (which appears opaque in the black and white image in FIG. 1, e-As$_4$S$_4$), whereas r-As$_4$S$_4$ mainly precipitated out at the bottom of the container, indicating hardly to dissolve in water.

Other embodiments were substantially similar, which will not be described detailed here.

Experimental Example 2: Dynamic Light Scattering (DLS) Analysis of Particle Size Distribution of e-As$_4$S$_4$ 20 mg of e-As$_4$S$_4$ powder of Example 4 was added in 1.25 mL of ddH$_2$O to prepare a suspended dispersion solution, and then 1 mL of the above dispersion solution was absorbed into a cuvette to analyze the particle size distribution using a Nano ZS90 Zetasizer instrument. The results were shown in FIG. 2.

Figure 2:
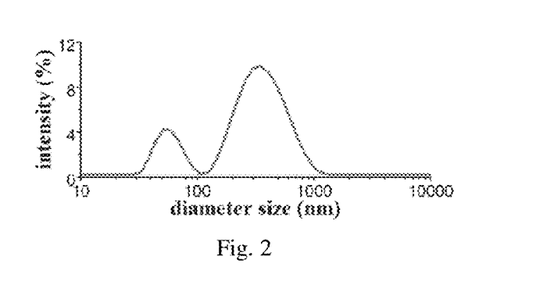
FIG. 2 is the particle size distribution diagram of the water-soluble realgar solid dispersion used in the present invention in the water phase.

The average hydrodynamic diameter of As$_4$S$_4$ nanoparticles in the dispersion solution was about 470 nm according to FIG. 2.

8 mg of the product of Embodiment 1, 10 mg of the product of Embodiment 2, 26 mg of the product of Embodiment 3, 4 mg of the product of Embodiment 4, 30 mg of the product of Embodiment 6, 32 mg of the product of Embodiment 8 and 6 mg of the product of Embodiment 10 (the $As_2S_2$ in the above samples is in the same amount) were weighted, respectively to be dissolved in 3 mL of saline. The dispersion solution of 1 mL was pipetted into a cuvette and tested by using a Nano ZS90 Zetasizer instrument. Results were shown in Table 2.

TABLE 2

The average hydrodynamic diameter of realgar colloidal particles in e-$As_4S_4$ aqueous dispersion

| Embodiments | Average hydrodynamic diameter of $As_4S_4$ particles (nm) |
| --- | --- |
| Embodiment 1 | 657.1 |
| Embodiment 2 | 546.0 |
| Embodiment 3 | 446.1 |
| Embodiment 4 | 689.9 |
| Embodiment 6 | 508.0 |
| Embodiment 8 | 400.0 |
| Embodiment 10 | 601.0 |

Experimental Example 2 to Experimental Example 8 of CN106236773A can be referred to for other physical and chemical properties of e-$As_4S_4$. For examples:

It was shown that the cumulative dissolution of $As_4S_4$ in the artificial gastric juice of the product of Embodiment 2, the product of Embodiment 7, the product of Embodiment 10 and the powder of Comparative Embodiment 1 was 25%, 16%, 9% and 0.2%, respectively. Compared with Comparative Embodiment 1 with the same $As_4S_4$ content, the cumulative dissolution of $As_4S_4$ in the artificial gastric juice of each of the Embodiments was greatly improved, and cumulative dissolution of $As_4S_4$ of Embodiment 2 was improved by 205 times as compared with Comparative Embodiment 1.

The cumulative dissolution of $As_4S_4$ in water in the present invention was significantly higher than that in the reported method (Guo T. The effect of solid dispersion technology on the stability and dissolution of nano realgar in vitro [J]. Chinese Journal of Traditional Chinese Medicine, 2013, 38(17): 2782-7.), indicating that e-$As_4S_4$ prepared by HME technology has unparalleled advantages and outstanding effects in improving the dissolution of $As_4S_4$ in water as compared with other methods. The cumulative dissolution of $As_4S_4$ of all embodiments in Table 1 in artificial gastric juice was similar and will not be described here.

From the determination of the total arsenic content in K562 cells, it is concluded that the realgar entering the water phase in the water-soluble realgar solid dispersion solution of the present invention will be taken up by K562 cells. Compared with Comparative Example 1 with the same $As_2S_2$ concentration, e-$As_4S_4$ of Embodiment 4 in the present invention could be taken up by K562 cells in a much larger amount, peaking after 12 h and then gradually decreasing, and the intracellular Arsenic content reached a stable level after 48 h, while $As_4S_4$ in Comparative Embodiment 1 was hardly taken up by the cells because little was in the aqueous phase.

According to the XRD analysis of realgar crystals in the water-soluble realgar solid dispersion, the pattern for Comparative Embodiment 1 showed a typical $As_2S_2$ crystal diffraction pattern with a stable baseline, indicating that the sample is a crystalline material. In the XRD pattern of Embodiment 5, diffraction peaks showed decreased intensity and broaden width, some crystal peaks for $As_2S_2$ even disappeared, the baseline of 10-15° was significantly elevated, and obvious amorphous diffuse reflection peaks appeared, indicating that part of the crystal structures were destroyed, and also suggesting the particle size was significantly reduced.

From the analysis of realgar nanoparticles dispersing status in the e-$As_4S_4$, it was found that the particle size of Comparative Embodiment 1 was relatively large, ranging from 25 to 75 μm. The cross section of the product of Embodiment 5 was smooth, and smaller $As_4S_4$ particles could be observed in the polymer matrix sporadically, indicating that after HME process, the large crystal particles of r-$As_4S_4$ were crushed and dispersed into the polymer matrix to form a realgar solid dispersion.

From the DLS analysis of the particle size distribution of the realgar colloidal particles in the aqueous dispersion of e-$As_4S_4$, it is concluded that the realgar in the products of each example can form colloidal particles with the polymer to form a stable dispersion. Particles in dispersion had three distribution peaks. Taking Embodiment 6 as an example, peak 1 was the micelles formed by polymer in the solution; peak 2 represented polymer-encapsulated realgar particles in the aqueous dispersion, with the hydrodynamic diameter ranging from 100 to 1000 nm and an average hydrodynamic diameter of 400-700 nm in a normal distribution; peak 3 was a distribution peak formed by a very small amount of realgar particles with a diameter larger than 1 μm in the solution. Comparing the test results of the product of Example 6 of the present invention in different dissolution media, it can be seen that Embodiment 6 had the largest relative number of polymer-encapsulated realgar particles in artificial gastric juice, followed by artificial intestinal fluid and saline, indicating that realgar in Embodiment 6 could quickly dissolve in physiological dissolution media, and the fastest dissolution rate was realized under acidic conditions in the stomach. The powder of Comparative Embodiment 1 could not be stably dispersed in an aqueous solution; the DLS method cannot be used for detection, so the DLS experimental data of Comparative Example 1 cannot be provided.

From the SEM analysis of the realgar colloidal particles in the water dispersion of the water-soluble realgar solid dispersion, it was found that the particle size of realgar particles in Embodiment 6 was significantly smaller than that of Comparative Embodiment 1, indicating that the HME process in the present invention effectively reduced the size of realgar particles to the submicron level.

In the determination of the bioavailability of a single oral administration in rats, it was shown that compared with Comparative Embodiment 1, Embodiment 8 significantly increased the arsenic content in the peripheral blood of rats by 4.41 times after oral administration and prolonged the circulation time of arsenic to maintain the blood arsenic content at a high level for a much longer time (70 hours), while blood arsenic metabolism was basically complete within 30 hours after oral administration in the rats of Comparative Embodiment 1. Similar results for bioavailability were obtained in the other embodiments as in Embodiment 8 and will not be described detailed here.

Experimental Example 3: The Effect of e-$As_4S_4$ on the Erythroid Differentiation in K562 Cells Experiment 1:

K562 cells are one of human chronic myeloid leukemia cell lines, which are bone marrow mononuclear cells with blocked erythroid differentiation. In this experiment, K562 cells were used to verify that they could be induced to differentiate towards erythrocytes by the inducer of the present invention.

K562 cells grown in their logarithmic phase were collected and seeded into 24-well culture plates at a density of $2\times10^5$ cells/mL with 500 μL per well. 20 mg of e-$As_4S_4$ of Embodiment 3 was dissolved in 1.25 mL of culture medium (a complete culture medium for K562 cell culture was prepared, which was a modified RPMI medium supplemented with 10% fetal bovine serum, 100 μg/mL penicillin and 100 μg/mL streptomycin. Fetal bovine serum was purchased from Gibco, Modified RPMI medium, penicillin and streptomycin were purchased from Hyclone) to form a dispersion that was added to the culture system and the final concentration of $As_4S_4$ in the medium was 0.1 mg/L, 0.5 mg/L, 1 mg/L, 2 mg/L, 3 mg/L, 4 mg/L. After incubation at 37° C. for 72 h, the mean fluorescence intensity of CD235a, a characteristic molecule of erythroid differentiation, was detected by flow cytometry, and results were shown in FIG. 3.

Figure 3:
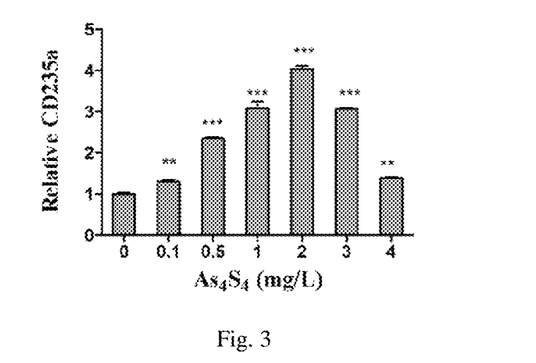
FIG. 3 is the diagram of influence of the water-soluble realgar solid dispersion used in the present invention on the erythroid differentiation of K562 cells.

FIG. 3 shows the change of CD235a after treatment with different concentrations of e-$As_4S_4$. The results indicated that e-$As_4S_4$ could significantly induce K562 cells to differentiate into erythroid at relatively low and medium concentrations; the e-$As_4S_4$ showed an unobvious cytotoxicity at low concentrations (<2 mg/L) mainly with an effect of inducing erythroid differentiation. At high concentrations (≥4 mg/L), e-$As_4S_4$ showed a significant cytotoxicity.

Similar effects were observed in the other embodiments and will not be described repeatedly here.

Experiment 2:

K562 cells grown in logarithmic phase were collected and seeded into the 24-well culture plates at a density of $2\times10^5$ cells/mL with 500 μL per well. 20 mg of e-$As_4S_4$ of Embodiment 3 or 20 mg of Embodiment 1 prepared with the approach provided in the patent CN1478486A was dissolved in 1.25 mL of the culture medium (same as Experiment 1) to form dispersion solutions that was added to the cell culture system, and the final concentration of realgar in the culture medium was 0.5 mg/L or 1 mg/L respectively. After incubated at 37° C. for 72 h, the mean fluorescence intensity of CD235a was detected by flow cytometry. Results were shown in FIG. 16.

Figure 16:
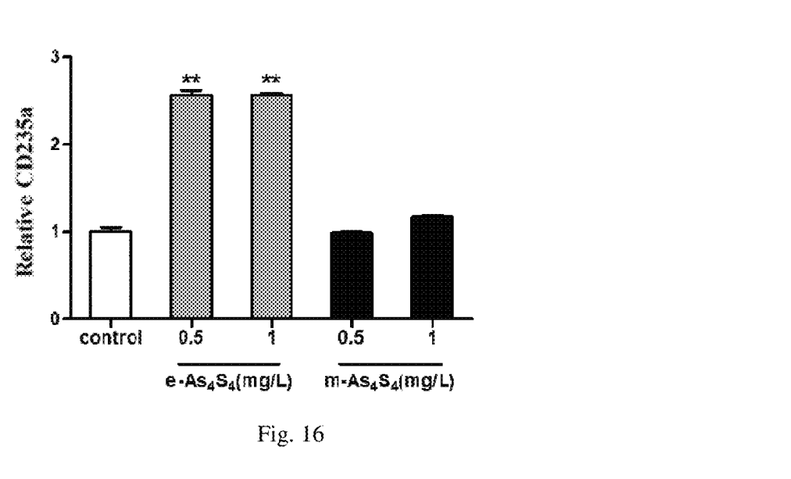
FIG. 16 is the water-soluble realgar solid dispersion used in the present invention and the realgar sample prepared by other methods affect the erythroid differentiation of K562 cells.

FIG. 16 shows the change of CD235a after treatment with realgar samples prepared with different concentrations of e-As4S4 or other methods. The results indicated that e-$As_4S_4$ significantly induced erythroid differentiation in K562 cells at relatively low and medium concentrations; while the realgar sample prepared according to the present patent application (as the representative of realgar) did not show the ability of inducing erythroid differentiation in K562 cells at the same concentration.

Similar effects were observed in the other embodiments and will not be described repeatedly here.

Experimental Example 4: The Effect of e-$As_4S_4$ on Myelodysplastic Syndrome (MDS)

Bone marrow mononuclear cells (BMMCs) were isolated from bone marrow samples from patients diagnosed with MDS and were seeded into the 24-well plates at a density of $5\times10^5$ cells/mL with 500 μL per well. 20 mg of e-$As_4S_4$ of Embodiment 3 was dissolved in 1.25 mL culture medium for bone marrow mononuclear cells (same as the culture medium in Experiment 1 of Experimental Example 3) to form a dispersion solution that was added to the culture system, and the final concentration of $As_4S_4$ was 0.5 mg/L, 1 mg/L, 2 mg/L, 4 mg/L, 8 mg/L. After incubated at 37° C. for 72 h, the proportion of CD235a positive BMMNCs was analyzed by flow cytometry. The results were shown in FIG. 4.

Figure 4:
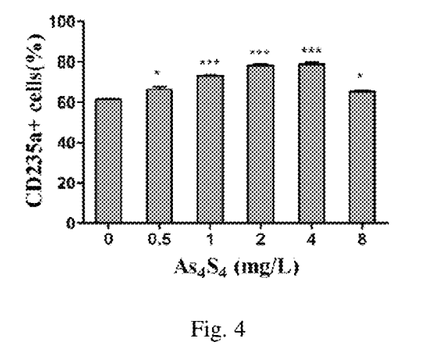
FIG. 4 is the influence diagram of the water-soluble realgar solid dispersion used in the present invention on MDS.

It was shown that e-$As_4S_4$ significantly increased the proportion of CD235a positive cells in the BMMNCs, indicating that e-$As_4S_4$ induced erythroid differentiation of bone marrow hematopoietic cells in BMMNCs, which meant that e-$As_4S_4$ could be used for the treatment of MDS by promoting the accumulation of erythrocytes in the bone marrow cells. The effect of erythroid differentiation induction was significant when the concentration was 1-4 mg/L, and the induction of differentiation was not toxic to the cells when the concentration did not exceed 8 mg/L. When the concentration exceeded 8 mg/L, the proportion of cells differentiating towards erythroid lineage decreased due to the apoptosis.

Similar effects were observed in the other embodiments and will not be described repeatedly here.

Although the concentration of e-$As_4S_4$ to induce erythroid differentiation was different for cells derived from different diseases, following experimental examples all shared the same regularity, that is, when the concentration was within a certain range (much lower than that in the patent application CN106236773A, where a large number of cells die, reaching the concentration of killing effect), e-$As_4S_4$ mainly played the role of inducing erythroid differentiation, not toxic to the cells; when the concentration exceeded a certain range, apoptosis began to occur, that is, starting to exert cell killing effect, and the proportion of cells that differentiate into erythroid decreases.

Experimental Example 5: The Effect of e-$As_4S_4$ on Myelodysplastic Syndrome-Refractory Anemia (MDS-RA)

BMMNCs were isolated from the bone marrow samples of patients diagnosed with MDS-RA. The sample processing and analysis were performed as the same as in Experimental Example 4. The results were shown in FIG. 5.

Figure 5:
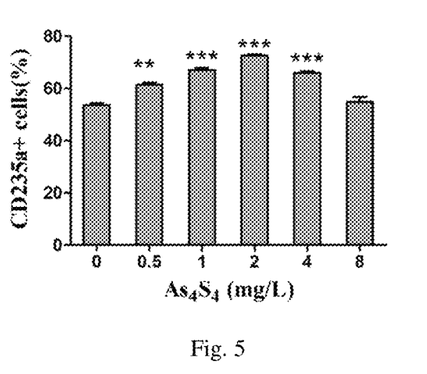
FIG. 5 is the influence diagram of the water-soluble realgar solid dispersion used in the present invention on MDS-RA.

It was shown in the results that e-$As_4S_4$ significantly increased the proportion of CD235a positive cells in the BMMNCs, indicating that e-$As_4S_4$ induced erythroid differentiation of bone marrow hematopoietic cells in BMMNCs, which meant that e-$As_4S_4$ could be used for the treatment of MDS-RA by promoting the accumulation of erythrocytes in the bone marrow cells and relieve refractory anemia. It had the effect of inducing differentiation when the concentration was 0.5-4 mg/L, and the induction of differentiation was not toxic to the cells when the concentration did not exceed 8 mg/L. When the concentration exceeded 8 mg/L, the proportion of cells towards erythroid differentiation decreased due to the apoptosis occurring.

Similar effects were observed in the other embodiments and will not be described repeatedly here.

Experimental Example 6: The Effect of e-$As_4S_4$ on Myelodysplastic Syndrome-Refractory Anemia with Ring-Shaped Iron Granulocytes (MDS-RARS)

BMMNCs were isolated from the bone marrow samples of patients diagnosed with MDS-RARS. The sample processing and analysis were performed as the same as in that Experimental Example 4. The results were shown in FIG. 6.

Figure 6:
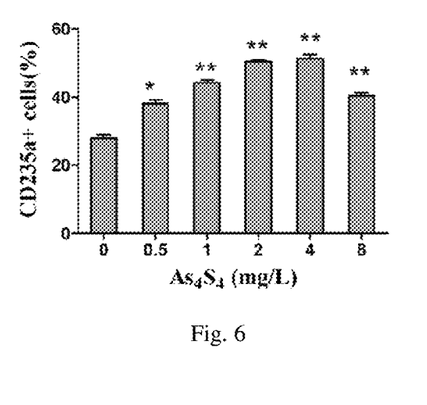
FIG. 6 is the influence diagram of the water-soluble realgar solid dispersion used in the present invention on MDS-RARS.

It was shown in results that e-$As_4S_4$ significantly increased the proportion of CD235a positive cells in the BMMNCs, indicating that e-$As_4S_4$ induced erythroid differentiation of bone marrow hematopoietic cells in BMMNCs, which meant that e-As$_4$S$_4$ could be used for the treatment of MDS-RA by promoting the accumulation of erythrocytes in the bone marrow cells. It had the effect of inducing differentiation when the concentration was 0.5-8 mg/L, and the induction of differentiation was not toxic to the cells when the concentration did not exceed 8 mg/L. When the concentration exceeded 8 mg/L, the proportion of cells towards erythroid differentiation decreased due to the apoptosis occurring.

Similar effects were observed in the other embodiments and will not be described repeatedly here.

Experimental Example 7: The Effect of e-As$_4$S$_4$ on Myelodysplastic Syndrome-Refractory Anemia with Blast Proliferation (MDS-RAEB)

BMMNCs were isolated from the bone marrow samples of patients diagnosed with MDS-RAEB. The sample processing and analysis were performed as the same as in Experimental Example 4. The results were shown in FIG. 7.

Figure 7:
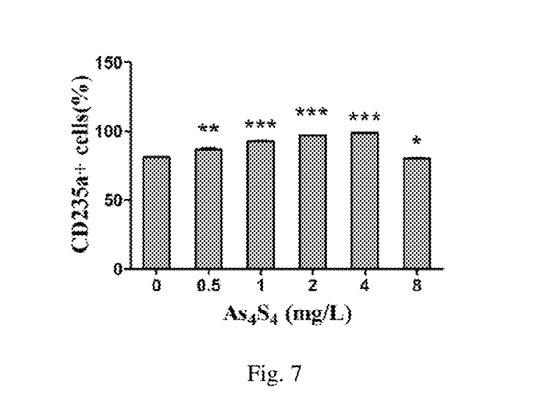
FIG. 7 is the influence diagram of the water-soluble realgar solid dispersion used in the present invention on MDS-RAEB.

It was shown in the results that e-As$_4$S$_4$ significantly increased the proportion of CD235a positive cells in the BMMNCs, indicating that e-As$_4$S$_4$ induced erythroid differentiation of bone marrow hematopoietic cells in BMMNCs, which meant that e-As$_4$S$_4$ could be used for the treatment of MDS-RAEB by promoting the accumulation of erythrocytes in the bone marrow cells. It had the effect of inducing differentiation when the concentration was 0.5-8 mg/L, and the induction of differentiation was not toxic to the cells when the concentration did not exceed 8 mg/L. When the concentration exceeded 8 mg/L, the proportion of cells towards erythroid differentiation decreased due to the apoptosis occurring.

Similar effects were observed in the other embodiments and will not be described repeatedly here.

Experimental Example 8: The Effect of e-As$_4$S$_4$ on the Transformation of Myelodysplastic Syndrome-Refractory Anemia with Blast Proliferation (MDS-RAEB-T)

BMMNCs were isolated from the bone marrow samples of patients diagnosed with MDS-RAEB-T. The sample processing and analysis were performed as the same as in Experimental Example 4. The results were shown in FIG. 8.

Figure 8:
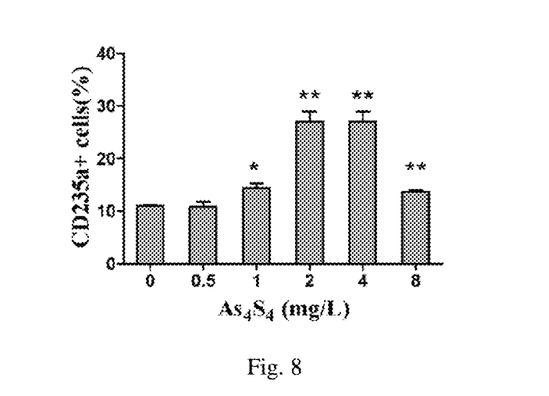
FIG. 8 is the influence diagram of the water-soluble realgar solid dispersion used in the present invention on MDS-RAEB-T.

It was shown in results that e-As$_4$S$_4$ significantly increased the proportion of CD235a positive cells in the BMMNCs, indicating that e-As$_4$S$_4$ induced erythroid differentiation of bone marrow hematopoietic cells in BMMNCs, which meant that e-As$_4$S$_4$ could be used for the treatment of MDS-RAEB-T by promoting the accumulation of erythrocytes in the bone marrow cells. It had the effect of inducing differentiation when the concentration was 1-8 mg/L, and the induction of differentiation was not toxic to the cells when the concentration did not exceed 8 mg/L. When the concentration exceeded 8 mg/L, the proportion of cells towards erythroid differentiation decreased due to the apoptosis occurring.

Similar effects were observed in the other embodiments and will not be described repeatedly here.

Experimental Example 9: The Effect of e-As$_4$S$_4$ on Chronic Myelomonocytic Leukemia (CMML)

BMMNCs were isolated from the bone marrow samples of patients diagnosed with CMML. The sample processing and analysis were performed as the same as in Experimental Example 4. The results were shown in FIG. 9.

Figure 9:
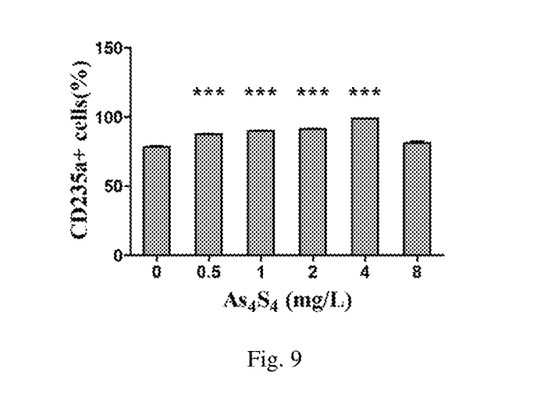
FIG. 9 is the influence diagram of the water-soluble realgar solid dispersion used in the present invention on CMML.

It was shown that e-As$_4$S$_4$ significantly increased the proportion of CD235a positive cells in the BMMNCs, indicating that e-As$_4$S$_4$ induced erythroid differentiation of bone marrow hematopoietic cells in BMMNCs, which meant that e-As$_4$S$_4$ could be used for the treatment of MDS-RA by promoting the accumulation of erythrocytes in the bone marrow cells. It had the effect of inducing differentiation when the concentration was 0.5-4 mg/L, and the induction of differentiation was not toxic to the cells when the concentration did not exceed 8 mg/L. When the concentration exceeded 8 mg/L, the proportion of cells towards erythroid differentiation decreased due to the apoptosis occurring.

Similar effects were observed in the other embodiments and will not be described repeatedly here.

Experimental Example 10: The Effect of e-As$_4$S$_4$ on Chronic Myeloproliferative Diseases BMMNCs were isolated from the bone marrow samples of patients diagnosed with chronic myeloproliferative diseases. The sample processing and analysis were performed as the same as in Experimental Example 4. The results were shown in FIG. 10.

Figure 10:
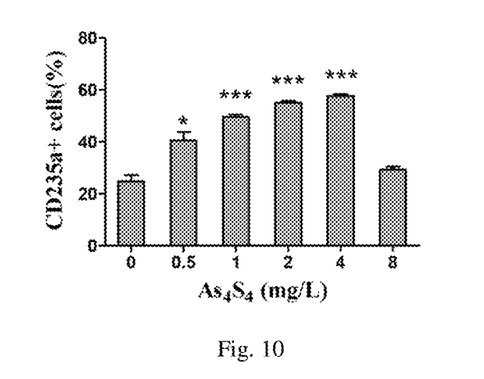
FIG. 10 is the influence diagram of the water-soluble realgar solid dispersion used in the present invention on chronic myeloproliferative diseases.

It was shown in the results that e-As$_4$S$_4$ significantly increased the proportion of CD235a positive cells in the BMMNCs, indicating that e-As$_4$S$_4$ induced erythroid differentiation of bone marrow hematopoietic cells in BMMNCs, which meant that e-As$_4$S$_4$ could be used for the treatment of chronic myeloproliferative diseases by promoting the accumulation of erythrocytes in the bone marrow cells. It had the effect of inducing differentiation when the concentration was 0.5-4 mg/L, and the induction of differentiation was not toxic to the cells when the concentration did not exceed 8 mg/L. When the concentration exceeded 8 mg/L, the proportion of cells towards erythroid differentiation decreased due to the apoptosis.

Similar effects were observed in the other embodiments and will not be described repeatedly here.

Experimental Example 11: The Effect of e-As$_4$S$_4$ on Chronic Myeloid Leukemia (CML)

BMMNCs were isolated from the bone marrow samples of patients diagnosed with CML. The sample processing and analysis were performed as the same as in Experimental Example 4. The results were shown in FIG. 11.

Figure 11:
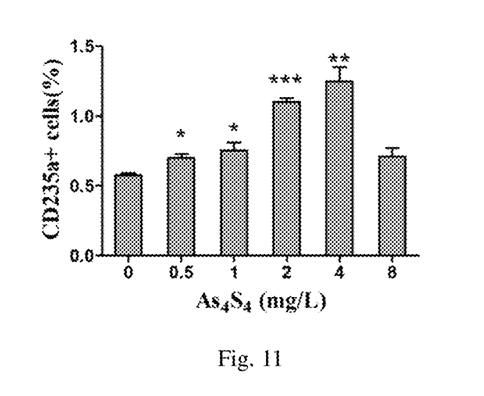
FIG. 11 is the influence diagram of the water-soluble realgar solid dispersion used in the present invention on CML.

It was shown in the results that e-As$_4$S$_4$ significantly increased the proportion of CD235a positive cells in the BMMNCs, indicating that e-As$_4$S$_4$ induced erythroid differentiation of bone marrow hematopoietic cells in BMMNCs, which meant that e-As$_4$S$_4$ could be used for the treatment of CML by promoting the accumulation of erythrocytes in the bone marrow cells. It had the effect of inducing differentiation when the concentration was 0.5-4 mg/L, and the induction of differentiation was not toxic to the cells when the concentration did not exceed 8 mg/L. When the concentration exceeded 8 mg/L, the proportion of cells towards erythroid differentiation decreased due to the apoptosis occurring.

Similar effects were observed in the other embodiments and will not be described repeatedly here.

Experimental Example 12: The Effect of e-As$_4$S$_4$ on Thrombocytosis

BMMNCs were isolated from the bone marrow samples of patients diagnosed with thrombocytosis. The sample processing and analysis were performed as the same as in Experimental Example 4. The results were shown in FIG. 12.

Figure 12:
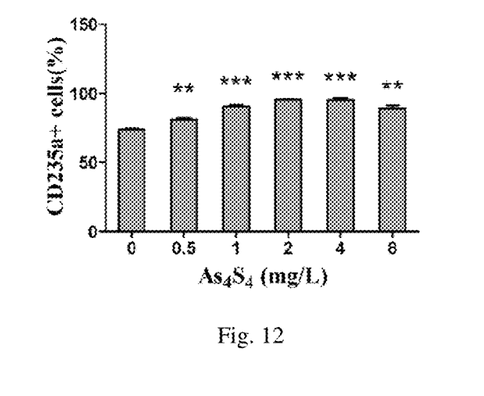
FIG. 12 is the influence diagram of the water-soluble realgar solid dispersion used in the present invention on thrombocytosis.

It was shown in the results that e-$As_4S_4$ significantly increased the proportion of CD235a positive cells in the BMMNCs, indicating that e-$As_4S_4$ induced erythroid differentiation of bone marrow hematopoietic cells in BMMNCs, which meant that e-$As_4S_4$ could be used for the treatment of thrombocytosis by promoting the accumulation of erythrocytes in the bone marrow cells. It had the effect of inducing differentiation when the concentration was 0.5-8 mg/L, and the induction of differentiation was not toxic to the cells when the concentration did not exceed 8 mg/L. When the concentration exceeded 8 mg/L, the proportion of cells towards erythroid differentiation decreased due to the apoptosis occurring.

Similar effects were observed in the other embodiments and will not be described repeatedly here.

Experimental Example 13: The Effect of e-$As_4S_4$ on Thrombocytopenia

BMMNCs were isolated from the bone marrow samples of patients diagnosed with thrombocytopenia. The sample processing and analysis were performed as the same as in Experimental Example 4. The results were shown in FIG. 13.

Figure 13:
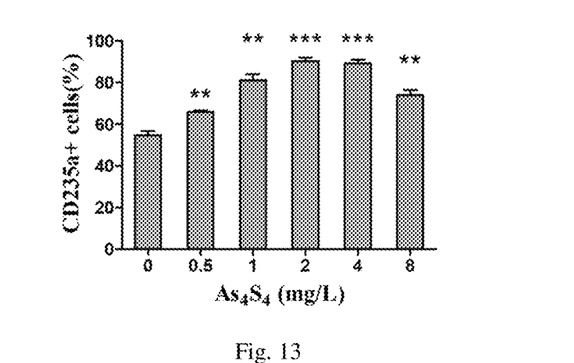
FIG. 13 is the influence diagram of the water-soluble realgar solid dispersion used in the present invention on thrombocytopenia.

It was shown in the results that e-$As_4S_4$ significantly increased the proportion of CD235a positive cells in the BMMNCs, indicating that e-$As_4S_4$ induced erythroid differentiation of bone marrow hematopoietic cells in BMMNCs, which meant that e-$As_4S_4$ could be used for the treatment of thrombocytopenia by promoting the accumulation of erythrocytes in the bone marrow cells. It had the effect of inducing differentiation when the concentration was 0.5-8 mg/L, and the induction of differentiation was not toxic to the cells when the concentrate on did not exceed 8 mg/L. When the concentration exceeded 8 mg/L, the proportion of cells towards erythroid differentiation decreased due to the apoptosis occurring.

Similar effects were observed in the other embodiments and will not be described repeatedly here.

Experimental Example 14: The Effect of e-$As_4S_4$ on Normal Bone Marrow

BMMNCs were isolated from the bone marrow samples of people without the diseases. The sample processing and analysis were performed as the same as in Experimental Example 4. The results were shown in FIG. 14.

Figure 14:
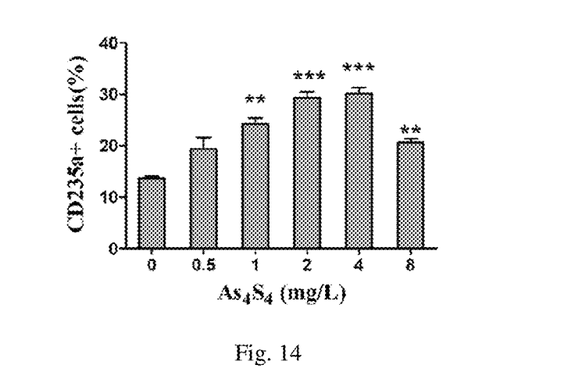
FIG. 14 is the influence diagram of the water-soluble realgar solid dispersion used in the present invention on normal bone marrow.

It was shown in the results that e-$As_4S_4$ significantly increased the proportion of CD235a positive cells in the BMMNCs, indicating that e-$As_4S_4$ induced erythroid differentiation of bone marrow hematopoietic cells in BMMNCs, which meant that e-$As_4S_4$ promote the accumulation of erythrocytes in the bone marrow cells. It had the effect of inducing differentiation when the concentration was 1-8 mg/L, and the induction of differentiation was not toxic to the cells when the concentration did not exceed 8 mg/L. When the concentration exceeded 8 mg/L, the proportion of cells towards erythroid differentiation decreased due to the apoptosis occurring.

Experimental Example 15: Cytotoxicity of e-$As_4S_4$

K562 cells grown in logarithmic phase were collected and seeded into the 96-well round bottom plates at a density of 2×10$^5$ cells/mL with 500 μL per well. 20 mg of e-$As_4S_4$ of Embodiment 2 was dissolved in 1.25 mL culture medium for K562 cells (same as the culture medium in Experiment 1 of Experimental sample 3) to form dispersion solution that was added to the culture system, and the final concentration of $As_4S_4$ was 1 mg/L, 1 mg/L, 2 mg/L, 4 mg/L and 8 mg/L. After incubated at 37° C. for 72 h, the plate was centrifuged, and the supernatant was removed and the cells were rinsed with PBS. 120 μL cell counting kit-8 (CCK-8) working solution was added to each well (CCK-8 working solution was obtained by mixing CCK8 stock solution and culture medium at a volume ratio of 1:10, and CCK8 stock solution was purchased from Dojindo Molecular Technologies). The cells were incubated at 37° C. in the dark for 1 h after mixed well. Afterwards, the plate was centrifuged and 90 μL of supernatant was absorbed in the microtiter plate, in which the absorbance at 450 nm and 630 nm (reference wavelength) was detected, and the cell viability was calculated according to the absorbance. The results were shown in FIG. 15.

Figure 15:
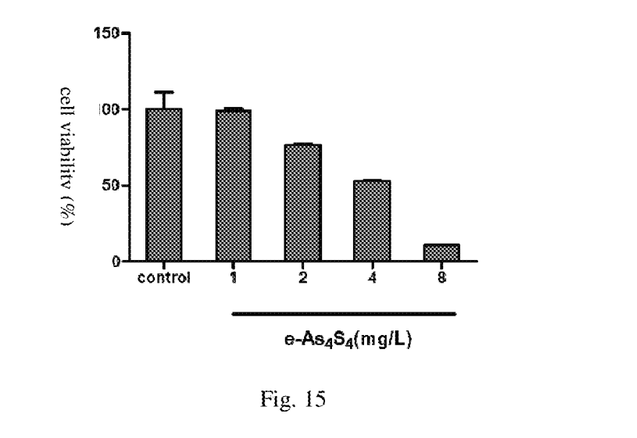
FIG. 15 is the cytotoxicity diagram of the water-soluble realgar solid dispersion used in the present invention on K562 cells.

It was shown in the results that the cytotoxicity of e-$As_4S_4$ at low concentration (<2 mg/L) was not significant, but significant at high concentration (≥4 mg/L).

INDUSTRIAL APPLICABILITY

The application of e-$As_4S_4$ provided by the present invention in preparing inducers for uses in the erythroid differentiation of bone marrow hematopoietic stem cells and/or progenitor cells can induce bone marrow hematopoietic stem cells and/or progenitor cells to differentiate towards erythrocytes, promote the accumulation of erythrocytes in bone marrow cells, and effectively relieve the decrease in the number of erythrocytes caused by blocked erythroid differentiation of bone marrow hematopoietic stem cells and/or progenitor cells, improve anemia caused by hematopoietic disorders, and meanwhile protect bone marrow cells from toxic chemotherapeutic drugs. Hence the application is suitable for industrial applications.

The invention claimed is:

1. A method of inducing erythroid differentiation of bone marrow hematopoietic stem cells and/or progenitor cells, the method comprising:
   contacting bone marrow hematopoietic stem cells and/or progenitor cells with an erythroid differentiation inducer, wherein the inducer comprises a water-soluble realgar solid dispersion having a realgar concentration from 0.1 mg/L to 8 mg/L and comprising 1 weight part of realgar, 1-20 weight parts of a polymer, and 0-5 weight parts of a surfactant.

2. The method of claim 1, wherein the realgar concentration is from 0.1 to mg/L to 4 mg/L.

3. A method of treating a disease caused by blocked erythroid differentiation of bone marrow hematopoietic stem cells and/or progenitor cells, the method comprising:
   administering an erythroid differentiation inducer to a patient having the disease, wherein the erythroid differentiation inducer comprises a water-soluble realgar solid dispersion having a realgar concentration from 0.1 mg/L to 8 mg/L and comprising 1 weight part of realgar, 1-20 weight parts of a polymer, and 0-5 weight parts of a surfactant.

4. The method of claim 3, wherein the realgar concentration is from 0.1 to mg/L to 4 mg/L.

* * * * *